United States Patent [19]
Eggerding

[11] Patent Number: 5,912,148
[45] Date of Patent: Jun. 15, 1999

[54] COUPLED AMPLIFICATION AND LIGATION METHOD

[75] Inventor: Faye Eggerding, San Francisco, Calif.

[73] Assignee: Perkin-Elmer Corporation Applied Biosystems, Foster City, Calif.

[21] Appl. No.: 08/975,902

[22] Filed: Sep. 19, 1996

Related U.S. Application Data

[63] Continuation of application No. 08/292,686, Aug. 19, 1994, abandoned.

[51] Int. Cl.$^6$ .......................... C12P 19/34; C07H 21/04; C07H 21/02; C12N 15/00
[52] U.S. Cl. .......................... 435/91.2; 435/6; 435/91.1; 435/810; 436/23.1; 436/24.3; 436/24.33; 436/25.3; 935/8; 935/76; 935/77
[58] Field of Search .............................. 435/6, 91.1, 91.2, 435/183, 810; 436/94, 800; 536/23.1, 23.5, 24.31, 24.33, 25.3, 25.32, 24.3; 935/5, 8, 76, 77

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,883,750 | 11/1989 | Whiteley et al. | 435/6 |
| 4,988,617 | 1/1991 | Landegren et al. | 435/6 |
| 5,407,769 | 4/1995 | Cutting et al. | 435/6 |
| 5,427,932 | 6/1995 | Weier et al. | 435/91.2 |

FOREIGN PATENT DOCUMENTS

| | | |
|---|---|---|
| WO 93/10267 | 5/1993 | WIPO . |
| WO93/20236 | 10/1993 | WIPO . |
| WO93/20239 | 10/1993 | WIPO . |
| WO 94/02648 | 2/1994 | WIPO . |
| 94/02648 | 3/1994 | WIPO . |

OTHER PUBLICATIONS

Nickerson et al, "Automated DNA diagnostics using an ELISA–based oligonucleotide ligation assay," Proc. Natl. Acad. Sci., 87: 8923–8927 (1990).
Landegren et al, "DNA diagnostics—molecular techniques and automation," Science, 242: 229–237 (1988).
Feero et al, "Hyperkalemic periodic paralysis: rapid molecular diagnosis and relationship of genotype to phenotype in 12 families," Neurology, 43: 668–673 (1993).
Wang et al, "Molecular genetic and genetic correlations in sodium channelopathies: lack of founder effect and evidence for a second gene," Am. J. Hum. Genet., 52: 1074–1084 (1993).
Eggerding et al, "Detection of mutations in the cystic fibrosis gene by multiplex amplification and oligonucleotide ligation," abstract, Am. J. Hum. Genet., 53: 1480 (1993).
Skolnick and Wallace, "Simultaneous analysis of multiple polymorphic loci using amplified sequence polymorphisms (ASPs)," Genomics, 2: 273–279 (1988).
Barany, "The ligase chain reaction in a PCR world," PCR Methods and Applications, 1: 2–16 (1991).
Winn–Deen et al, "Sensitive fluorescence method for detecting DNA ligation amplification products," Clinical Chemistry, 37: 1522–1523 (1991).
Landegren et al, "A ligase–mediated gene detection technique," Science, 241: 1077–1080 (1988).
Weisberg et al, "Simultaneous mutagenesis of multiple sites: application of the ligase chain reaction using PCR products instead of oligonucleotides," Biotechniques, 15: 68–75 (1993).
Barany, "Genetic disease detection and DNA amplification using cloned thermostable ligase," Proc. Natl. Acad. Sci., 88: 189–193 (1991).
Brinson et al, "PCR 14–plex for cystic fibrosis," p. 238, abstract, Pediatric Pulmonology, Supplement 9, Sep., 1993.
Eggerding et al, "Cystic fibrosis mutation detection by oligonucleotide ligation," abstract, Pediatric Pulmonology, Supplement 9, p. 240, Sep., 1993.
Winn–Deen et al, "Multiplex analysis of CFTR mutations using the oligonucleotide ligation assay (OLA) and sequence–coded separation," p. 240, abstract, Pediatric Pulmonology, Supplement 9, Sep., 1993.
Prchal et al, "Transcriptional analysis of the active X–chromosome in normal and clonal hematopoiesis," Blood, 81: 269–271 (1993).
Wiedmann et al, "Discrimination of *Listeria monocytogenes* from other Listeria species by ligase chain reaction," Applied and Environmental Microbiology, 58: 3443–3447 (1992).
Wiedmann et al, "Detection of *Listeria monocytogenes* with a nonisotopic polymerase chain reaction–coupled ligase chain reaction assay," Applied and Environmental Microbiology, 59: 2743–2745 (1993).
Eggerding, F., A One–Step Coupled Amplification and Oligonucleotide Ligation Procedure for Multiplex Genetic Typing; PCR Methods & Appls., 4(1995) Jun., No., 6, New York, US.
Nickerson, D., "Automated DNA diagnostics using an ELISA–based oligonucleotide ligation assay", 6039 Proceedings of the National Academy of Sciences, 87 (1990), Nov., No. 22, Washington, D.C. US.
Weidmann et al., "Detection of mutations in the cystic fibrosis gene by multiplex amplification and oligonucleotide ligation," The American Journal of Human Genetics, vol. 53, No. 3, Supplement, abstract #1485, Sep. 1993.

(List continued on next page.)

Primary Examiner—Bradley L. Sisson
Attorney, Agent, or Firm—Wilson Sonsini Goodrich & Rosati

[57] ABSTRACT

A method based on polymerase chain reaction (PCR) amplification and oligonucleotide ligase assay (OLA) reaction is provided for analyzing complex genetic systems in a single reaction vessel. The method involves simultaneously incubating a sample containing one or more target polynucleotides with PCR primers and OLA probes in a single reaction mixture. The presence of variant polynucleotide sequences in the sample is determined by detecting and identifying the products of the OLA reaction.

34 Claims, 2 Drawing Sheets

OTHER PUBLICATIONS

Barany, "Genetic disease detection and DNA amplification using cloned thermostable ligase," *PNAS, USA*, vol. 88, pp. 189–193.

Sambrook et alii, eds., *Molecualr Cloning A Laboratory Manual*, 2nd. ed., Cold Spring Harbor Laboratory Press 1989, pp. 9.50–9.51, and 11.46–11.49.

Eggerding et alii, "Detection of mutations in the cystic fibrosis gene by multiplex amplification and oligonucleotide ligation," *The American Journal of Human Genetics*, vol. 53, No. 3, Supplement, Sep. 1993, abstract #1485.

Wiedmann et alii, "Detection of *Listeria monocytogenes* with a Nonisotopic Polymerase Chain Reaction–Coipled Ligase Chain Reaction Assay," *Applied and Environmental Microbiology*, Aug. 1993, pp. 2743–2745.

```
                          SEQUENCE LISTING (1) GENERAL INFORMATION:

(iii) NUMBER OF SEQUENCES:   75

(2) INFORMATION FOR SEQ ID NO: 1:

(i) SEQUENCE CHARACTERISTICS:
          (A) LENGTH: 27 nucleotides
          (B) TYPE: nucleic acid
          (C) STRANDEDNESS: single
          (D) TOPOLOGY: linear (xi) SEQUENCE DESCRIPTION: SEQ ID NO: 1:

AGAGTTTCAA CATATGGTAT GACCCTC                                              27

(2) INFORMATION FOR SEQ ID NO: 2:

(i) SEQUENCE CHARACTERISTICS:
          (A) LENGTH: 27 nucleotides
          (B) TYPE: nucleic acid
          (C) STRANDEDNESS: single
          (D) TOPOLOGY: linear (xi) SEQUENCE DESCRIPTION: SEQ ID NO: 2:

CCCTTACTTG TACCAGCTCA CTACCTA                                              27

(2) INFORMATION FOR SEQ ID NO: 3:

(i) SEQUENCE CHARACTERISTICS:
          (A) LENGTH: 31 nucleotides
          (B) TYPE: nucleic acid
          (C) STRANDEDNESS: single
          (D) TOPOLOGY: linear
```

(xi) SEQUENCE DESCRIPTION: SEQ ID NO: 3:

GTGCATAGCA GAGTACCCGA AACAGGAAGT A                     31

(2) INFORMATION FOR SEQ ID NO:4:

(i) SEQUENCE CHARACTERISTICS:
        (A) LENGTH: 31 nucleotides
        (B) TYPE: nucleic acid
        (C) STRANDEDNESS: single
        (D) TOPOLOGY: linear (xi) SEQUENCE DESCRIPTION: SEQ ID NO: 4:

TGATCCATTC ACAGTAGCTT ACCCATAGAG G                     31

(2) INFORMATION FOR SEQ ID NO:5:

(i) SEQUENCE CHARACTERISTICS:
        (A) LENGTH: 37 nucleotides
        (B) TYPE: nucleic acid
        (C) STRANDEDNESS: single
        (D) TOPOLOGY: linear (xi) SEQUENCE DESCRIPTION: SEQ ID NO: 5:

CAACTGTGGT TAAAGCAATA GTGTGATTAT ATGATTA                37

(2) INFORMATION FOR SEQ ID NO:6:

(i) SEQUENCE CHARACTERISTICS:
        (A) LENGTH: 36 nucleotides
        (B) TYPE: nucleic acid
        (C) STRANDEDNESS: single
        (D) TOPOLOGY: linear (xi) SEQUENCE DESCRIPTION: SEQ ID NO: 6:

GCACAGATTC TGAGTAACCA TAATCTCTAC CAAATC                 36

(2) INFORMATION FOR SEQ ID NO:7:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear (xi) SEQUENCE DESCRIPTION: SEQ ID NO: 7:

CATCACAAAT AATAGTACTT AGAACACCTA GTACAGCTGC T           41

(2) INFORMATION FOR SEQ ID NO:8:

(i) SEQUENCE CHARACTERISTICS:
        (A) LENGTH: 34 nucleotides
        (B) TYPE: nucleic acid
        (C) STRANDEDNESS: single
        (D) TOPOLOGY: linear (xi) SEQUENCE DESCRIPTION: SEQ ID NO: 8:

GCCCTGAACT CCTGGGCTCA AGTGATCCTC CTGC                   34

(2) INFORMATION FOR SEQ ID NO:9:

(i) SEQUENCE CHARACTERISTICS:
        (A) LENGTH: 42 nucleotides
        (B) TYPE: nucleic acid
        (C) STRANDEDNESS: single
        (D) TOPOLOGY: linear (xi) SEQUENCE DESCRIPTION: SEQ ID NO: 9:

```
AATTATAATC ACCTTGTGGA TCTAAATTTC AGTTGACTTG TC                          42

(2) INFORMATION FOR SEQ ID NO:10:

(i) SEQUENCE CHARACTERISTICS:
        (A) LENGTH: 42 nucleotides
        (B) TYPE: nucleic acid
        (C) STRANDEDNESS: single
        (D) TOPOLOGY: linear (xi) SEQUENCE DESCRIPTION: SEQ ID NO: 10:

TTTAAGACAT ACCCTAAATC TAAGTCAGTG TTTTCTAATA AC                          42

(2) INFORMATION FOR SEQ ID NO:11:

(i) SEQUENCE CHARACTERISTICS:
        (A) LENGTH: 28 nucleotides
        (B) TYPE: nucleic acid
        (C) STRANDEDNESS: single
        (D) TOPOLOGY: linear (xi) SEQUENCE DESCRIPTION: SEQ ID NO: 11:

GCCCGACAAA TAACCAAGTG ACAAATAG                                          28

(2) INFORMATION FOR SEQ ID NO:12:

(i) SEQUENCE CHARACTERISTICS:
        (A) LENGTH: 26 nucleotides
        (B) TYPE: nucleic acid
        (C) STRANDEDNESS: single
        (D) TOPOLOGY: linear (xi) SEQUENCE DESCRIPTION: SEQ ID NO: 12:

GCTAACACAT TGCTTCAGGC TACTGG                                            26

(2) INFORMATION FOR SEQ ID NO:13:

(i) SEQUENCE CHARACTERISTICS:
        (A) LENGTH: 41 nucleotides
        (B) TYPE: nucleic acid
        (C) STRANDEDNESS: single
        (D) TOPOLOGY: linear (xi) SEQUENCE DESCRIPTION: SEQ ID NO: 13:

GGTCAGGATT GAAAGTGTGC AACAAGGTTT GAATGAATAA G                           41

(2) INFORMATION FOR SEQ ID NO:14:

(i) SEQUENCE CHARACTERISTICS:
        (A) LENGTH: 40 nucleotides
        (B) TYPE: nucleic acid
        (C) STRANDEDNESS: single
        (D) TOPOLOGY: linear (xi) SEQUENCE DESCRIPTION: SEQ ID NO: 14:

CTATGAGAAA ACTGCACTGG AGAAAAAAAA GACAGCAATG                             40

(2) INFORMATION FOR SEQ ID NO:15:

(i) SEQUENCE CHARACTERISTICS:
        (A) LENGTH: 38 nucleotides
        (B) TYPE: nucleic acid
        (C) STRANDEDNESS: single
        (D) TOPOLOGY: linear (xi) SEQUENCE DESCRIPTION: SEQ ID NO: 15:

AATGTTCACA AGGGACTCCA AATATTGCYG AGTATTTG                               38
```

(2) INFORMATION FOR SEQ ID NO:16:

(i) SEQUENCE CHARACTERISTICS:
        (A) LENGTH: 40 nucleotides
        (B) TYPE: nucleic acid
        (C) STRANDEDNESS: single
        (D) TOPOLOGY: linear (xi) SEQUENCE DESCRIPTION: SEQ ID NO: 16:

TCCAGTCAAA AGTACCTGTT GCTCCAGGTA TGTTAGGGTA                              40

(2) INFORMATION FOR SEQ ID NO:17:

(i) SEQUENCE CHARACTERISTICS:
        (A) LENGTH: 43 nucleotides
        (B) TYPE: nucleic acid
        (C) STRANDEDNESS: single
        (D) TOPOLOGY: linear (xi) SEQUENCE DESCRIPTION: SEQ ID NO: 17:

AAAAAAAAAA AAAAAAAAAA GGCACCATTA AGAAAATAT CAT                          43

(2) INFORMATION FOR SEQ ID NO:18:

(i) SEQUENCE CHARACTERISTICS:
        (A) LENGTH: 25 nucleotides
        (B) TYPE: nucleic acid
        (C) STRANDEDNESS: single
        (D) TOPOLOGY: linear (xi) SEQUENCE DESCRIPTION: SEQ ID NO: 18:

AAGGCACCAT TAAAGAAAAT ATCAT                                              25

(2) INFORMATION FOR SEQ ID NO:19:

(i) SEQUENCE CHARACTERISTICS:
        (A) LENGTH: 19 nucleotides
        (B) TYPE: nucleic acid
        (C) STRANDEDNESS: single
        (D) TOPOLOGY: linear (xi) SEQUENCE DESCRIPTION: SEQ ID NO: 19:

GTGTGATTCC ACCTTCTCA                                                     19

(2) INFORMATION FOR SEQ ID NO:20:

(i) SEQUENCE CHARACTERISTICS:
        (A) LENGTH: 23 nucleotides
        (B) TYPE: nucleic acid
        (C) STRANDEDNESS: single
        (D) TOPOLOGY: linear (xi) SEQUENCE DESCRIPTION: SEQ ID NO: 20:

TAAAGAAATT CTTGCTCGTT GAT                                                23

(2) INFORMATION FOR SEQ ID NO:21:

(i) SEQUENCE CHARACTERISTICS:
        (A) LENGTH: 29 nucleotides
        (B) TYPE: nucleic acid
        (C) STRANDEDNESS: single
        (D) TOPOLOGY: linear (xi) SEQUENCE DESCRIPTION: SEQ ID NO: 21:

AAAAAAATAT CACTCCAAAG GCTTTCCTT                                          29

(2) INFORMATION FOR SEQ ID NO:22:

(i) SEQUENCE CHARACTERISTICS:
        (A) LENGTH: 34  nucleotides
        (B) TYPE: nucleic acid
        (C) STRANDEDNESS:  single
        (D) TOPOLOGY:  linear (xi) SEQUENCE DESCRIPTION: SEQ ID NO:  22:

CCCCCCTATT TTTTCTGGAA CATTTAGAAA AAAG                                      34

(2) INFORMATION FOR SEQ ID NO:23:

(i) SEQUENCE CHARACTERISTICS:
        (A) LENGTH: 39  nucleotides
        (B) TYPE: nucleic acid
        (C) STRANDEDNESS:  single
        (D) TOPOLOGY:  linear (xi) SEQUENCE DESCRIPTION: SEQ ID NO:  23:

AAAAAAAAAA AAAAGAGTAC TTTGTTATCA GCTTTTTTT                                 39

(2) INFORMATION FOR SEQ ID NO:24:

(i) SEQUENCE CHARACTERISTICS:
        (A) LENGTH: 50  nucleotides
        (B) TYPE: nucleic acid
        (C) STRANDEDNESS:  single
        (D) TOPOLOGY:  linear (xi) SEQUENCE DESCRIPTION: SEQ ID NO:  24:

AAAAAAAAAA AAAAAAAAAA AAAAAACATC TGTTGCAGTA ATAAAATGGT                     50

(2) INFORMATION FOR SEQ ID NO:25:

(i) SEQUENCE CHARACTERISTICS:
        (A) LENGTH: 15  nucleotides
        (B) TYPE: nucleic acid
        (C) STRANDEDNESS:  single
        (D) TOPOLOGY:  linear (xi) SEQUENCE DESCRIPTION: SEQ ID NO:  25:

CTGGCCAGAG GGTGG                                                           15

(2) INFORMATION FOR SEQ ID NO:26:

(i) SEQUENCE CHARACTERISTICS:
        (A) LENGTH: 19  nucleotides
        (B) TYPE: nucleic acid
        (C) STRANDEDNESS:  single
        (D) TOPOLOGY:  linear (xi) SEQUENCE DESCRIPTION: SEQ ID NO:  26:

CCAACAGAAG GTAAACCTA                                                       19

(2) INFORMATION FOR SEQ ID NO:27:

(i) SEQUENCE CHARACTERISTICS:
        (A) LENGTH: 24  nucleotides
        (B) TYPE: nucleic acid
        (C) STRANDEDNESS:  single
        (D) TOPOLOGY:  linear (xi) SEQUENCE DESCRIPTION: SEQ ID NO:  27:

AAACTAGATA AATCGCGATA GAGT                                                 24

(2) INFORMATION FOR SEQ ID NO:28:

(i) SEQUENCE CHARACTERISTICS:

```
        (A) LENGTH: 25 nucleotides
        (B) TYPE: nucleic acid
        (C) STRANDEDNESS: single
        (D) TOPOLOGY: linear (xi) SEQUENCE DESCRIPTION: SEQ ID NO: 28:

AAATTTCAGA TGCGATCTGT GAGCT                                              25

(2) INFORMATION FOR SEQ ID NO:29:

(i) SEQUENCE CHARACTERISTICS:
        (A) LENGTH: 27 nucleotides
        (B) TYPE: nucleic acid
        (C) STRANDEDNESS: single
        (D) TOPOLOGY: linear (xi) SEQUENCE DESCRIPTION: SEQ ID NO: 29:

AAAAAATCTG CAAACTTGGA GATGTCT                                            27

(2) INFORMATION FOR SEQ ID NO:30:

(i) SEQUENCE CHARACTERISTICS:
        (A) LENGTH: 35 nucleotides
        (B) TYPE: nucleic acid
        (C) STRANDEDNESS: single
        (D) TOPOLOGY: linear (xi) SEQUENCE DESCRIPTION: SEQ ID NO: 30:

AAAAAAAAAT ATGTTTAGTT TGATTTATAA GAAGT                                   35

(2) INFORMATION FOR SEQ ID NO:31:

(i) SEQUENCE CHARACTERISTICS:
        (A) LENGTH: 42 nucleotides
        (B) TYPE: nucleic acid
        (C) STRANDEDNESS: single
        (D) TOPOLOGY: linear (xi) SEQUENCE DESCRIPTION: SEQ ID NO: 31:

AAAAAAAAAA AAAAAAAAAA TTGCTAAAGA AATTCTTGCT CA                           42

(2) INFORMATION FOR SEQ ID NO:32:

(i) SEQUENCE CHARACTERISTICS:
        (A) LENGTH: 45 nucleotides
        (B) TYPE: nucleic acid
        (C) STRANDEDNESS: single
        (D) TOPOLOGY: linear (xi) SEQUENCE DESCRIPTION: SEQ ID NO: 32:

CCCCCCCCCC CCCCCCCCCC CCCCCCACAA TAGGACATGG AATAT                        45

(2) INFORMATION FOR SEQ ID NO:33:

(i) SEQUENCE CHARACTERISTICS:
        (A) LENGTH: 45 nucleotides
        (B) TYPE: nucleic acid
        (C) STRANDEDNESS: single
        (D) TOPOLOGY: linear (xi) SEQUENCE DESCRIPTION: SEQ ID NO: 33:

AAAAAAAAAA AAAAAAAAAA ACACCATTAA AGAAATATC ATCTT                         45

(2) INFORMATION FOR SEQ ID NO:34:

(i) SEQUENCE CHARACTERISTICS:
        (A) LENGTH: 27 nucleotides
        (B) TYPE: nucleic acid
```

(C) STRANDEDNESS:  single
        (D) TOPOLOGY:  linear (xi) SEQUENCE DESCRIPTION: SEQ ID NO: 34:

AAACACCATT AAAGAAAATA TCATCTT                                               27

(2) INFORMATION FOR SEQ ID NO:35:

(i) SEQUENCE CHARACTERISTICS:
        (A) LENGTH: 17  nucleotides
        (B) TYPE: nucleic acid
        (C) STRANDEDNESS:  single
        (D) TOPOLOGY:  linear (xi) SEQUENCE DESCRIPTION: SEQ ID NO: 35:

GTGATTCCAC CTTCTCC                                                          17

(2) INFORMATION FOR SEQ ID NO:36:

(i) SEQUENCE CHARACTERISTICS:
        (A) LENGTH: 25 nucleotides
        (B) TYPE: nucleic acid
        (C) STRANDEDNESS:  single
        (D) TOPOLOGY:  linear (xi) SEQUENCE DESCRIPTION: SEQ ID NO: 36:

AATAAAGAAA TTCTTGCTCG TTGAC                                                 25

(2) INFORMATION FOR SEQ ID NO:37:

(i) SEQUENCE CHARACTERISTICS:
        (A) LENGTH: 27 nucleotides
        (B) TYPE: nucleic acid
        (C) STRANDEDNESS:  single
        (D) TOPOLOGY:  linear (xi) SEQUENCE DESCRIPTION: SEQ ID NO: 37:

AAAAATATCA CTCCAAAGGC TTTCCTC                                               27

(2) INFORMATION FOR SEQ ID NO:38:

(i) SEQUENCE CHARACTERISTICS:
        (A) LENGTH: 32 nucleotides
        (B) TYPE: nucleic acid
        (C) STRANDEDNESS:  single
        (D) TOPOLOGY:  linear (xi) SEQUENCE DESCRIPTION: SEQ ID NO: 38:

CCCCTATTTT TTCTGGAACA TTTAGAAAAA AC                                         32

(2) INFORMATION FOR SEQ ID NO:39:

(i) SEQUENCE CHARACTERISTICS:
        (A) LENGTH: 36 nucleotides
        (B) TYPE: nucleic acid
        (C) STRANDEDNESS:  single
        (D) TOPOLOGY:  linear (xi) SEQUENCE DESCRIPTION: SEQ ID NO: 39:

AAAAAAAAAA AAGAGTACTT TGTTATCAGC TTTTTT                                     36

(2) INFORMATION FOR SEQ ID NO:40:

(i) SEQUENCE CHARACTERISTICS:
        (A) LENGTH: 48 nucleotides
        (B) TYPE: nucleic acid
        (C) STRANDEDNESS:  single
        (D) TOPOLOGY:  linear (xi) SEQUENCE DESCRIPTION: SEQ ID NO: 40:

AAAAAAAAAA AAAAAAAAAA AAAAAATCTG TTGCAGTAAT AAAATGGC                48

(2) INFORMATION FOR SEQ ID NO:41:

(i) SEQUENCE CHARACTERISTICS:
        (A) LENGTH: 17 nucleotides
        (B) TYPE: nucleic acid
        (C) STRANDEDNESS: single
        (D) TOPOLOGY: linear (xi) SEQUENCE DESCRIPTION: SEQ ID NO: 41:

ACCTGGCCAG AGGGTGA                                                  17

(2) INFORMATION FOR SEQ ID NO:42:

(i) SEQUENCE CHARACTERISTICS:
        (A) LENGTH: 21 nucleotides
        (B) TYPE: nucleic acid
        (C) STRANDEDNESS: single
        (D) TOPOLOGY: linear (xi) SEQUENCE DESCRIPTION: SEQ ID NO: 42:

AACAACAGAA GGTAAACCTA C                                             21

(2) INFORMATION FOR SEQ ID NO:43:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (xi) SEQUENCE DESCRIPTION: SEQ ID NO: 43:

ACTAGATAAA TCGCGATAGA GC                                            22

(2) INFORMATION FOR SEQ ID NO:44:

(i) SEQUENCE CHARACTERISTICS:
        (A) LENGTH: 23 nucleotides
        (B) TYPE: nucleic acid
        (C) STRANDEDNESS: single
        (D) TOPOLOGY: linear (xi) SEQUENCE DESCRIPTION: SEQ ID NO: 44:

ATTTCAGATG CGATCTGTGA GCC                                           23

(2) INFORMATION FOR SEQ ID NO:45:

(i) SEQUENCE CHARACTERISTICS:
        (A) LENGTH: 25 nucleotides
        (B) TYPE: nucleic acid
        (C) STRANDEDNESS: single
        (D) TOPOLOGY: linear (xi) SEQUENCE DESCRIPTION: SEQ ID NO: 45:

AAAATCTGCA AACTTGGAGA TGTCC                                         25

(2) INFORMATION FOR SEQ ID NO:46:

(i) SEQUENCE CHARACTERISTICS:
        (A) LENGTH: 33 nucleotides
        (B) TYPE: nucleic acid
        (C) STRANDEDNESS: single
        (D) TOPOLOGY: linear (xi) SEQUENCE DESCRIPTION: SEQ ID NO: 46:

AAAAAAATAT GTTTAGTTTG ATTTATAAGA AGG                                33

(2) INFORMATION FOR SEQ ID NO:47:

(i) SEQUENCE CHARACTERISTICS:
        (A) LENGTH: 39 nucleotides
        (B) TYPE: nucleic acid
        (C) STRANDEDNESS: single
        (D) TOPOLOGY: linear (xi) SEQUENCE DESCRIPTION: SEQ ID NO: 47:

AAAAAAAAAA AAAAAAAATG CTAAAGAAAT TCTTGCTCG                          39

(2) INFORMATION FOR SEQ ID NO:48:

(i) SEQUENCE CHARACTERISTICS:
        (A) LENGTH: 47 nucleotides
        (B) TYPE: nucleic acid
        (C) STRANDEDNESS: single
        (D) TOPOLOGY: linear (xi) SEQUENCE DESCRIPTION: SEQ ID NO: 48:

CCCCCCCCCC CCCCCCCCCC CCCCCCCAC AATAGGACAT GGAATAC                  47

(2) INFORMATION FOR SEQ ID NO:49:

(i) SEQUENCE CHARACTERISTICS:
        (A) LENGTH: 29 nucleotides
        (B) TYPE: nucleic acid
        (C) STRANDEDNESS: single
        (D) TOPOLOGY: linear (xi) SEQUENCE DESCRIPTION: SEQ ID NO: 49:

ATTTCTGCCT AGATGCTGGG AAATAAAAC                                     29

(2) INFORMATION FOR SEQ ID NO:50:

(i) SEQUENCE CHARACTERISTICS:
        (A) LENGTH: 26 nucleotides
        (B) TYPE: nucleic acid
        (C) STRANDEDNESS: single
        (D) TOPOLOGY: linear (xi) SEQUENCE DESCRIPTION: SEQ ID NO: 50:

CCAGGAAAAC TCCGCCTTTC CAGTTG                                        26

(2) INFORMATION FOR SEQ ID NO:51:

(i) SEQUENCE CHARACTERISTICS:
        (A) LENGTH: 28 nucleotides
        (B) TYPE: nucleic acid
        (C) STRANDEDNESS: single
        (D) TOPOLOGY: linear (xi) SEQUENCE DESCRIPTION: SEQ ID NO: 51:

CTCTAGAGAC CATGCTCAGA TCTTCCAT                                      28

(2) INFORMATION FOR SEQ ID NO:52:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (xi) SEQUENCE DESCRIPTION: SEQ ID NO: 52:

GCAAAGTTCA TTAGAACTGA TCTATTGACT                                    30

(2) INFORMATION FOR SEQ ID NO:53:

(i) SEQUENCE CHARACTERISTICS:
       (A) LENGTH: 29 nucleotides
       (B) TYPE: nucleic acid
       (C) STRANDEDNESS: single
       (D) TOPOLOGY: linear (xi) SEQUENCE DESCRIPTION: SEQ ID NO: 53:

TATACAGTGT AATGGATCAT GGGCCATGT                     29

(2) INFORMATION FOR SEQ ID NO:54:

(i) SEQUENCE CHARACTERISTICS:
       (A) LENGTH: 29 nucleotides
       (B) TYPE: nucleic acid
       (C) STRANDEDNESS: single
       (D) TOPOLOGY: linear (xi) SEQUENCE DESCRIPTION: SEQ ID NO: 54:

GTGCAAGATA CAGTGTTGAA TGTGGTGCA                     29

(2) INFORMATION FOR SEQ ID NO:55:

(i) SEQUENCE CHARACTERISTICS:
       (A) LENGTH: 36 nucleotides
       (B) TYPE: nucleic acid
       (C) STRANDEDNESS: single
       (D) TOPOLOGY: linear (xi) SEQUENCE DESCRIPTION: SEQ ID NO: 55:

GTGAATCGAT GTGGTGACCA TATTGTAATG CATGTA             36

(2) INFORMATION FOR SEQ ID NO:56:

(i) SEQUENCE CHARACTERISTICS:
       (A) LENGTH: 36 nucleotides
       (B) TYPE: nucleic acid
       (C) STRANDEDNESS: single
       (D) TOPOLOGY: linear (xi) SEQUENCE DESCRIPTION: SEQ ID NO: 56:

ACCATGCTAC ATTCTGCCAT ACCAACAATG GTGAAC             36

(2) INFORMATION FOR SEQ ID NO:57:

(i) SEQUENCE CHARACTERISTICS:
       (A) LENGTH: 34 nucleotides
       (B) TYPE: nucleic acid
       (C) STRANDEDNESS: single
       (D) TOPOLOGY: linear (xi) SEQUENCE DESCRIPTION: SEQ ID NO: 57:

CTCATGGGAT GTGATTCTTT CGACCAATTT AGTG               34

(2) INFORMATION FOR SEQ ID NO:58:

(i) SEQUENCE CHARACTERISTICS:
       (A) LENGTH: 33 nucleotides
       (B) TYPE: nucleic acid
       (C) STRANDEDNESS: single
       (D) TOPOLOGY: linear (xi) SEQUENCE DESCRIPTION: SEQ ID NO: 58:

AGAATCTGGT ACTAAGGACA GCCTTCTCTC TAA                33

(2) INFORMATION FOR SEQ ID NO:59:

(i) SEQUENCE CHARACTERISTICS:
        (A) LENGTH: 36 nucleotides
        (B) TYPE: nucleic acid
        (C) STRANDEDNESS: single
        (D) TOPOLOGY: linear (xi) SEQUENCE DESCRIPTION: SEQ ID NO: 59:

GAATGGGATA GAGAGCTGGC TTCAAAGAAA AATCCT                         36

(2) INFORMATION FOR SEQ ID NO:60:

(i) SEQUENCE CHARACTERISTICS:
        (A) LENGTH: 39 nucleotides
        (B) TYPE: nucleic acid
        (C) STRANDEDNESS: single
        (D) TOPOLOGY: linear (xi) SEQUENCE DESCRIPTION: SEQ ID NO: 60:

CCTTTATATT TTTACACCTA TTCACCAGAT TTCGTAGTC                      39

(2) INFORMATION FOR SEQ ID NO:61:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (xi) SEQUENCE DESCRIPTION: SEQ ID NO: 61:

TGGTGTTTCC TATGATGAAT TA                                       22

(2) INFORMATION FOR SEQ ID NO:62:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (xi) SEQUENCE DESCRIPTION: SEQ ID NO: 62:

AAGAACTATA TTGTCTTTCT CT                                       22

(2) INFORMATION FOR SEQ ID NO:63:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (xi) SEQUENCE DESCRIPTION: SEQ ID NO: 63:

CTCCACTCAG TGTGATTCCA                                        20

(2) INFORMATION FOR SEQ ID NO:64:

(i) SEQUENCE CHARACTERISTICS:
        (A) LENGTH: 24 nucleotides
        (B) TYPE: nucleic acid
        (C) STRANDEDNESS: single
        (D) TOPOLOGY: linear (xi) SEQUENCE DESCRIPTION: SEQ ID NO: 64:

CACTGTTGCA AAGTTATTGA ATCC                                24

(2) INFORMATION FOR SEQ ID NO:65:

(i) SEQUENCE CHARACTERISTICS:
        (A) LENGTH: 23 nucleotides
        (B) TYPE: nucleic acid
        (C) STRANDEDNESS: single
        (D) TOPOLOGY: linear (xi) SEQUENCE DESCRIPTION: SEQ ID NO: 65:

TTGGATCCCT ATGAACAGTG GAG                                            23

(2) INFORMATION FOR SEQ ID NO:66:

(i) SEQUENCE CHARACTERISTICS:
        (A) LENGTH: 23 nucleotides
        (B) TYPE: nucleic acid
        (C) STRANDEDNESS: single
        (D) TOPOLOGY: linear (xi) SEQUENCE DESCRIPTION: SEQ ID NO: 66:

GAGACTACTG AACACTGAAG GAG                                            23

(2) INFORMATION FOR SEQ ID NO:67:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (xi) SEQUENCE DESCRIPTION: SEQ ID NO: 67:

GAGTAAGACA CCCTGAAAGG AA                                             22

(2) INFORMATION FOR SEQ ID NO:68:

(i) SEQUENCE CHARACTERISTICS:
        (A) LENGTH: 19 nucleotides
        (B) TYPE: nucleic acid
        (C) STRANDEDNESS: single
        (D) TOPOLOGY: linear (xi) SEQUENCE DESCRIPTION: SEQ ID NO: 68:

GATTTGAACA CTGCTTGCT                                                 19

(2) INFORMATION FOR SEQ ID NO:69:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (xi) SEQUENCE DESCRIPTION: SEQ ID NO: 69:

CAAGTCAACC AAACCATACA                                                20

(2) INFORMATION FOR SEQ ID NO:70:

(i) SEQUENCE CHARACTERISTICS:
        (A) LENGTH: 21 nucleotides
        (B) TYPE: nucleic acid
        (C) STRANDEDNESS: single
        (D) TOPOLOGY: linear (xi) SEQUENCE DESCRIPTION: SEQ ID NO: 70:

GTTCCTCCTT GTTATCCGGG T                                              21

(2) INFORMATION FOR SEQ ID NO:71:

(i) SEQUENCE CHARACTERISTICS:
        (A) LENGTH: 24 nucleotides (B) TYPE: nucleic acid
        (C) STRANDEDNESS: single
        (D) TOPOLOGY: linear (xi) SEQUENCE DESCRIPTION: SEQ ID NO: 71:

GAGTCTTTAA GTTCATTGAC ATGC                                                  24

(2) INFORMATION FOR SEQ ID NO:72:

(i) SEQUENCE CHARACTERISTICS:
        (A) LENGTH: 26 nucleotides
        (B) TYPE: nucleic acid
        (C) STRANDEDNESS: single
        (D) TOPOLOGY: linear (xi) SEQUENCE DESCRIPTION: SEQ ID NO: 72:

TATTACCAAA AATAGAAAAT TAGAGA                                                26

(2) INFORMATION FOR SEQ ID NO:73:

(i) SEQUENCE CHARACTERISTICS:
        (A) LENGTH: 22 nucleotides
        (B) TYPE: nucleic acid
        (C) STRANDEDNESS: single
        (D) TOPOLOGY: linear (xi) SEQUENCE DESCRIPTION: SEQ ID NO: 73:

TAATACTTCC TTGCACAGGC CC                                                    22

(2) INFORMATION FOR SEQ ID NO:74:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (xi) SEQUENCE DESCRIPTION: SEQ ID NO: 74:

TTGACCTCCA CTCAGTGTGA                                                       20

(2) INFORMATION FOR SEQ ID NO:75:

(i) SEQUENCE CHARACTERISTICS:
        (A) LENGTH: 19 nucleotides
        (B) TYPE: nucleic acid
        (C) STRANDEDNESS: single
        (D) TOPOLOGY: linear (xi) SEQUENCE DESCRIPTION: SEQ ID NO: 75:

TCACTTTCCA AGGAGCCAC                                                        19

COUPLED AMPLIFICATION AND LIGATION METHOD

This application is a continuation of application Ser. No. 08/292,686, filed Aug. 19, 1994, now abandoned.

The present invention relates generally to methods of detecting and/or distinguishing known DNA sequence variants. More specifically, the invention pertains to a method of performing DNA amplification reactions and oligonucleotide ligase assay reactions in a single reaction vessel with minimal post-amplification sample manipulation to detect and/or distinguish known DNA sequence variants.

BACKGROUND

Nucleic acid sequence analysis has become important in many research, medical, and industrial fields, e.g. Caskey, Science 236: 1223–1228 (1987); Landegren et al, Science, 242: 229–237 (1988); and Arnheim et al, Ann. Rev. Biochem., 61: 131–156 (1992). In large part, the strong interest in nucleic acid analysis has been driven by the development of several methods for amplifying target nucleic acids, e.g. polymerase chain reaction (PCR), ligation chain reaction (LCR), and the like, e.g. Kessler, editor, Nonradioactive Labeling and Detection of Biomolecules (Springer-Verlag, Berlin, 1992); Innis et al, editors, PCR Protocols (Academic Press, New York 1990); Barany, PCR Methods and Applications 1: 5–16 (1991). While such amplification techniques have the potential of providing highly sensitive and specific diagnostic assays, there is still a need to make assays utilizing such techniques convenient to perform in a clinical or field setting, especially when they involve the analysis of complex genetic systems, such as the extremely variable cystic fibrosis locus, or other highly polymorphic loci. In such systems, identifying the amplified product poses a special problem whose solution typically requires multiple post-amplification manipulations. A promising approach for identifying polynucleotides in such systems is the oligonucleotide ligation assay (OLA), Whiteley et al, U.S. Pat. No. 4,883,750. In this assay approach, oligonucleotides are prepared that are complementary to adjacent regions of a target sequence. The oligonucleotides are capable of hybridizing to the target so that they lie end-to-end and can be ligated when no mismatches occur at or near the contiguous ends. Whenever such mismatches do occur, then ligation is precluded. As a result, a set of oligonucleotide pairs may be provided which are perfect complements of all the allelic variants of interest at a given locus. By a judicious selection of labeling methodologies, a wide range of alleles, either from the same of different loci, can be specifically identified in a single assay.

Unfortunately, application of OLA to amplified target sequences complicates the assay, as exemplified by Nickerson et al., Proc. Natl. Acad. Sci. USA 87:8923–8927 (1990), which discloses the amplification of target DNAs by PCR and discrimination of variant DNA by OLA. After PCR amplification of the target DNA was performed in a first set of 96-well cluster plates, aliquots of the amplified samples were transferred to a second set of 96-well plates for OLA and the generation of ligation products. Aliquots of samples containing the ligation products were then transferred form the second set of plates to a third set of 96-well plates for detection of ligation products by an ELISA-based procedure.

The application of DNA-based assays employing amplification and OLA detection would be greatly facilitated if the number manipulations required to implement the assays could be reduced.

SUMMARY OF THE INVENTION

The present invention provides a method of amplifying and detecting by OLA in the same reaction vessel one or more target polynucleotides in a sample. An important aspect of the invention is providing primers, or oligonucleotides (in the case of ligation-based amplification), for target polynucleotide amplification having a higher annealing temperature than that of the oligonucleotides employed in the OLA. In this manner, the target polynucleotides is amplified at a temperature above the annealing temperature of the oligonucleotides employed in the OLA, thereby avoiding the interference to chain extension and/or ligation that would occur were the oligonucleotides allowed to anneal to the target polynucleotides during amplification.

Generally, the method of the invention comprises the steps of (a) providing a plurality of amplification primers, each amplification primer being capable of annealing to one or more target polynucleotides at a first annealing temperature, (b) providing a plurality of oligonucleotide probes, each oligonucleotide probe of the plurality being capable of annealing to the target polynucleotides at a second annealing temperature, such that substantially none of the oligonucleotide probes anneal to the target polynucleotide at the first annealing temperature, (c) amplifying the target polynucleotides using the plurality of amplification primers at a temperature greater than or equal to the first annealing temperature; (d) ligating oligonucleotide probes of the plurality that specifically hybridize to the one or more target polynucleotides at a temperature equal to or less than the second annealing temperature to form one or more ligation products; and (e) detecting the one or more ligation products. The presence or absence of the ligation products is then correlated to the presence or absence of the one or more target polynucleotides in the sample.

The invention further includes kits for carrying out the method of the invention. Preferably, such kits include (a) a plurality of amplification primers, each amplification primer of the plurality being capable of annealing to one or more target polynucleotides at a first annealing temperature; (b) a plurality of oligonucleotide probes, each oligonucleotide probe being capable of annealing to the target polynucleotides at a second annealing temperature, such that substantially none of the oligonucleotide probes anneal to the target polynucleotide at the first annealing temperature; (c) means for amplifying the target polynucleotides using the plurality of amplification primers at a temperature greater than or equal to the first annealing temperature; and (d) means for ligating oligonucleotide probes at a temperature equal to or less than the second annealing temperature to form one or more ligation products.

The invention overcomes a deficiency attendant to current approaches by permitting the amplification and detection by OLA in a single reaction vessel, thereby reducing the amount of sample and reagent manipulations required in such an assay. The method of the invention is readily automated. Generally, the method can be used to assay, simultaneously, target sequences, such as sequences associated with a mixture of pathogen specimens, gene sequences in a genomic DNA fragment mixture, highly polymorphic or mutationally complex genetic loci, such as the cystic fibrosis locus, p53 locus, ras locus, or the like.

DEFINITIONS

Figure 1:
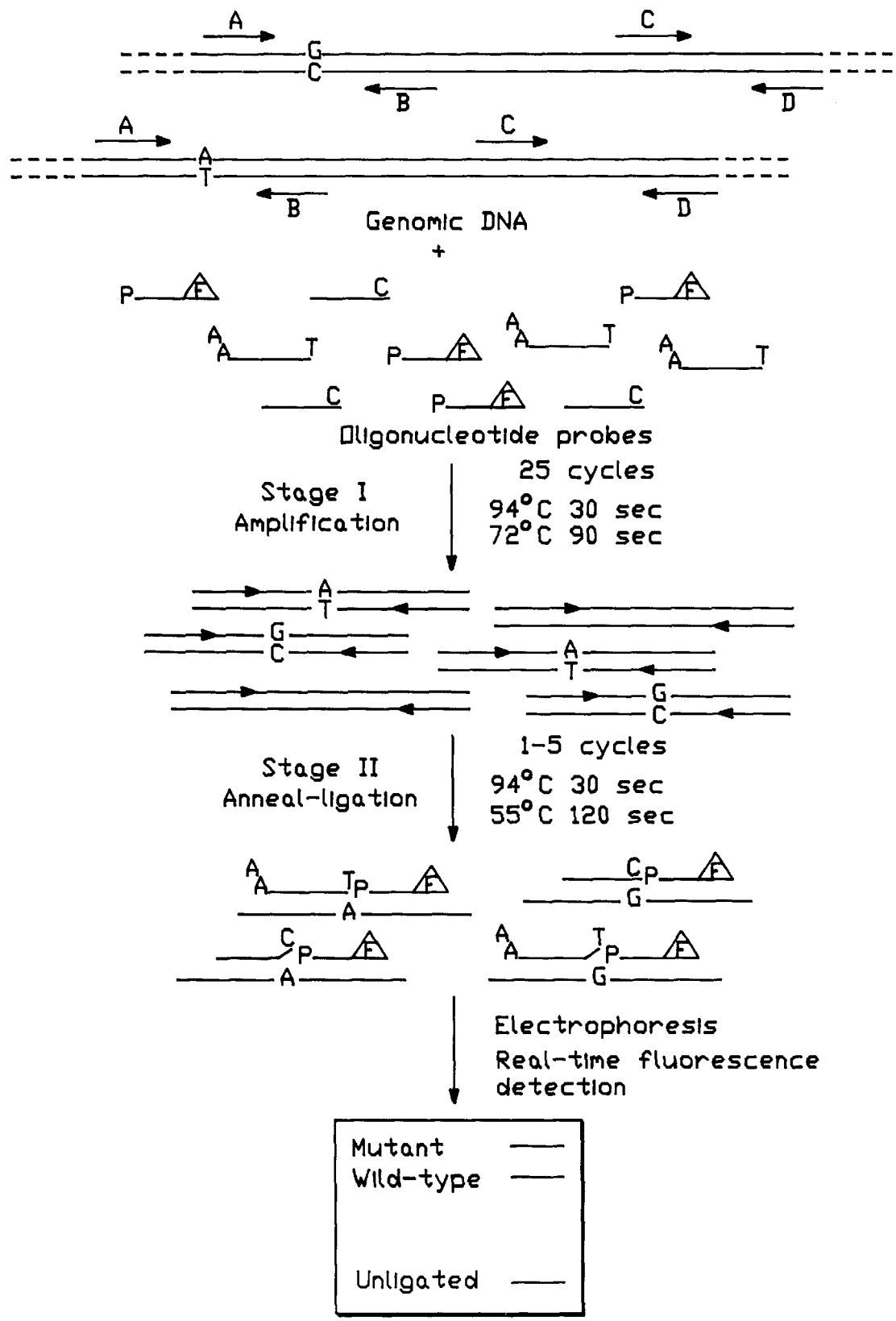
FIG. 1 is a schematic representation of one embodiment of the invention.

As used in reference to the method of the invention, the term "target polynucleotide" in the plural includes both multiple separate polynucleotide strands and multiple regions on the same polynucleotide strand that are separately amplified and/or detected. A target polynucleotide may be a single molecule of double-stranded or single-stranded polynucleotide, such as a length of genomic DNA, cDNA or viral genome including RNA, or a mixture of polynucleotide fragments, such as genomic DNA fragments or a mixture of viral and somatic polynucleotide fragments from an infected sample. Typically, a target polynucleotide is double-stranded DNA which is denatured, e.g., by heating, to form single-stranded target molecules capable of hybridizing with primers and/or oligonucleotide probes.

The term "oligonucleotide" as used herein includes linear oligomers of natural or modified monomers or linkages, including deoxyribonucleosides, ribonucleosides, polyamide nucleic acids, and the like, capable of specifically binding to a target polynucleotide by way of a regular pattern of monomer-to-monomer interactions, such as Watson-Crick type of base pairing, and capable of being ligated to another oligonucleotide in a template-driven reaction. Usually monomers are linked by phosphodiester bonds or analogs thereof to form oligonucleotides ranging in size from a few monomeric units, e.g. 3–4, to several hundreds of monomeric units. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The term "polynucleotide" as used herein usually means a linear oligomer of nucleosides or analogs thereof, including deoxyribonucleosides, ribonucleosides, and the like, from a few tens of units in length to many thousands of units in length.

As used herein, "pluality" in reference to oligonucleotide probes includes sets of two or more oligonucleotide probes where there may be a single "common" oligonucleotide probe that is usually specific for a non-variable region of a target polynucleotide and one or more "wild-type" and/or "mutant" oligonucleotide probes that are usually specific for a region of a target polynucleotide that contains allelic or mutational variants in sequence.

As used herein, "nucleoside" includes the natural nucleosides, including 2'-deoxy and 2'-hydroxyl forms, e.g. as described in Komberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543–584 (1990); or the like. Such analogs include synthetic nucleosides designed to enhance binding properties, reduce degeneracy, increase specificity, and the like.

The term "amplification primer", as used herein, refers to an oligonucleotide which either (i) acts to initiate synthesis of a complementary DNA strand when placed under conditions in which synthesis of a primer extension product is induced, i.e., in the presence of nucleotides and a polymerization-inducing agent such as a DNA-dependent DNA polymerase and at suitable temperature, pH, metal concentration, and salt concentration, or (ii) is ligated to another amplification primer in a ligation-based amplification scheme.

DETAILED DESCRIPTION OF THE INVENTION

The invention eliminates the need to provide separate reaction mixture and/or vessels for applying OLA to amplified target polynucleotides. In accordance with the method, target polynucleotides are amplified above a first temperature (i.e., the first annealing temperature) in the presence of the oligonucleotide probes of the OLA. At or above this first temperature, the OLA components of the reaction mixture do not interfere with amplification. After amplification, the temperature of the reaction mixture is lowered to a second temperature (i.e., the second annealing temperature) that permits specific annealing of the oligonucleotide probes of the OLA to the target polynucleotides. The reaction mixture then may be cycled between the second temperature and a higher temperature to permit linear amplification of ligation products.

Preferably, amplification primers are from 30 to 50 nucleotide long and have Tm's between 80° C. and 120° C. Preferably, such amplification primers are employed with a first annealing temperature of between about 72° C. to about 84° C. More preferably, the first annealing temperature is between about 72° C. to about 75° C. Preferably, the oligonucleotide probes used in the OLA are from 8 to 30 nucleotides long and have Tm's between 40° C. and 70° C. Such oligonucletide probes are preferably used with a second annealing temperature between about 30° C. to about 55° C., and more preferably, between about 40° C. to about 55° C. Preferably, annealing temperatures are selected to ensure specificity in amplification and detection. Typically, annealing temperatures are selected in the range of from 1–2° C. above or below the melting temperature of an amplification primer or oligonucleotide probe to about 5–10° C. below such temperature. Guidance for selecting appropriate primers or oligonucleotides given these design constraints and the nature of the polynucleotide targets can be found in many references, including Rychlik et al. (1989) Nucl. Acids. Res. 17:8453–8551; Lowe et al. (1990) Nucl. Acids Res. 18: 1757–1761; Hiller et al. (1991) PCR Methods and Applications 1:124–128; Wetmur, Critical Reviews in Biochemistry and Molecular Biology, 26: 227–259 (1991); Breslauer et al, Proc. Natl. Acad. Sci. 83: 3746–3750 (1986); Innis et al, editors, PCR Protocols (Academic Press, New York, 1990); and the like.

Amplification primers and oligonucleotide probes for OLA reactions are readily synthesized by standard techniques, e.g., solid phase synthesis via phosphoramidite chemistry, as disclosed in U.S. Pat. Nos. 4,458,066 and 4,415,732 to Caruthers et al; Beaucage et al. (1992) Tetrahedron 48:2223–2311; and Applied Biosystems User Bulletin No. 13 (Apr. 1, 1987). Likewise, the primers and oligonucleotide probes are derivatized with reactive groups, e.g. for attaching labels, using conventional chemistries, such as disclosed in Eckstein, editor, Oligonucleotides and Analogues: A Practical Approach (IRL Press, Oxford, 1991).

Ligation products generated in the method are detected by a variety of means. For example, detection may be achieved by coupling a detectable label to the terminus of one of the oligonucleotide probes. Alternatively, the non-ligating termini of the oligonucletides may be labeled with distinct labels which are detectable by spectroscopic, photochemical, biochemical, immunochemical or radiochemical means. Detection may also be achieved by using a nucleic acid hybridization assay, e.g. as described in Urdea et al, U.S. Pat. No. 5,124,246; or like techniques.

Preferably, ligation products bear mobility modifiers. i.e., extensions which allow the mobility of each ligation product to be defined so that they may be distinguished by methods which provide size dependent separation, such as sedimentation, exclusion chromatography, filtration, high performance liquid chromatography, electrophoresis, affinity collection, or the like. Most preferably, such mobility modifiers alter the electrophoretic mobility of the ligation products rendering them separately detectable. Preferably, the wild type allele OLA products are separated from mutant allele OLA products by electrophoresis or capillary electrophoresis, particularly gel-free capillary electrophoresis. More preferably, amplified OLA products containing mobility modifiers are detectably labeled and separated by gel electrophoresis on an instrument such as a model 373 DNA Sequencer (Applied Biosystems, Foster City, Calif.), described in the following references: Mayrand et al. (1990) Clin. Chem. 36:2063–2071; and Mayrand et al. (1992) Appl. Theoret. Electrophoresis 3:1–11. Synthesizing and attaching mobility modifiers to oligonucleotides and their use in OLA is described in International applications PCT/US93/20236 and PCT/US93/20239, which are incorporated by reference.

As taught in these applications, a variety of mobility modifying elements are attached to oligonucleotide probes, including polymer chains formed of polyethylene oxide, polyglycolic acid, polylactic acid, polypeptide, oligosaccharide, polyurethane, polyamids, polysulfonamide, polysulfoxide, and block copolymers thereof, including polymers composed of units of multiple subunits linked by charged or uncharged linking groups.

An important feature of this embodiment of the invention is the use of different mobility modifying polymer chains for imparting different ratios of charge/translational frictional drag to different ligation products. That is, the ratio of combined charge/combined translational frictional drag of the oligonucleotide, attached polymer chain, and label, as measured at a given pH and with respect to electrophoretic polymer movement through a non-sieving liquid medium, is different for each different-sequence ligation product. Preferably, the distinctive ratio of charge/translational frictional drag is typically achieved by differences in the lengths (number of subunits) of the polymer chain. However, differences in polymer chain charge are also contemplated, as are differences in oligonucleotide length.

More generally, the polymers forming the polymer chain may be homopolymers, random copolymers, or block copolymers, and the polymer may have a linear, comb, branched, or dendritic architecture. In addition, although the invention is described herein with respect to a single polymer chain attached to an associated binding polymer at a single point, the invention also contemplates binding polymers which are derivatized by more than one polymer chain element, where the elements collectively form the polymer chain.

Preferred polymer chains are those which are hydrophilic, or at least sufficiently hydrophilic when bound to the oligonucleotide binding polymer to ensure that the probe is readily soluble in aqueous medium. The polymer chain should also not effect the hybridization reaction. Where the binding polymers are highly charged, as in the case of oligonucleotides, the binding polymers are preferably uncharged or have a charge/subunit density which is substantially less than that of the binding polymer.

Methods of synthesizing selected-length polymer chains, either separately or as part of a single-probe solid-phase synthetic method, are described below, along with preferred properties of the polymer chains.

In one preferred embodiment, described below, the polymer chain is formed of hexaethylene oxide (HEO) units, where the HEO units are joined end-to-end to form an unbroken chain of ethylene oxide subunits, or are joined by charged or uncharged linkages, as described below.

Methods of preparing polymer chains in the probes generally follow known polymer subunit synthesis methods. These methods, which involve coupling of defined-size, multi-subunit polymer units to one another, either directly or through charged or uncharged linking groups, are generally applicable to a wide variety of polymers, such as polyethylene oxide, polyglycolic acid, polylactic acid, polyurethane polymers, and oligosaccharides.

The methods of polymer unit coupling are suitable for synthesizing selected-length copolymers, e.g., copolymers of polyethylene oxide units alternating with polypropylene units. Polypeptides of selected lengths and amino acid composition, either homopolymer or mixed polymer, can be synthesized by standard solid-phase methods. Preferably, PEO chains having a selected number of HEO units are prepared from DMT-protected phosphoramidite monomers, as disclosed in Levenson et al, U.S. Pat. No. 4,914,210.

Coupling of the polymer chains to an oligonucleotide can be carried out by an extension of conventional phosphoramidite oligonucleotide synthesis methods, or by other standard coupling methods. Alternatively, the polymer chain can be built up on an oligonucleotide (or other sequence-specific binding polymer) by stepwise addition of polymer-chain units to the oligonucleotide, using standard solid-phase synthesis methods.

As noted above, the polymer chain imparts to its probe, a ratio of charge/translational frictional drag which is distinctive for each different-sequence probe and/or ligation product. The contribution which the polymer chain makes to the derivatized binding polymer will in general depend on the subunit length of the polymer chain. However, addition of charge groups to the polymer chain, such as charged linking groups in the PEO chain, or charged amino acids in a polypeptide chain, can also be used to achieve selected charge/frictional drag characteristics in the probe.

An important feature of this embodiment of the invention is providing ligation products of different-length and/or different-sequence oligonucleotides which can be finely resolved electrophoretically in a non-sieving medium by derivatization with polymer chains having slightly different size and/or charge differences. Electrophoresis, such as capillary electrophoresis, (CE) is carried out by standard methods, and using conventional CE equipment.

The ability to fractionate charged binding polymers, such as oligonucleotides, by electrophoresis in the absence of a sieving matrix offers a number of advantages. One of these is the ability to fractionate charged polymers all having about the same size. This feature allows the oligonucleotide moiety of the probes to have similar sizes, and thus similar hybridization kinetics and thermodynamics with the target polynucleotide. Another advantage is the greater convenience of electrophoresis, particularly CE, where sieving polymers and particularly problems of forming and removing crosslinked gels in a capillary tube are avoided.

In the above OLA, the concentration of ligation product can be enhanced, if necessary, by repeated probe hybridization and ligation steps. Simple linear amplification can be achieved using the target polynucleotide as a template and repeating the denaturation, annealing, and probe ligation steps until a desired concentration of derivatized probe is reached.

In order to carry out the method of the invention, then, a sample is provided which includes DNA containing one or more target nucleotide sequences. Chromosomal DNA of an individual who is being tested or screened is obtained from a cell sample from that individual. Cell samples can be obtained from a variety of tissues depending on the age and condition of the individual. Preferably, cell samples are obtained from peripheral blood using well known techniques. In fetal testing, a sample is preferably obtained by amniocentesis or chorionic villi sampling. Other sources of DNA include semen, buccal cells, or the like. Preferably, DNA is extracted from the sample using standard procedures, e.g., phenol:chloroform extraction as described by Maniatis et al., supra, and Higuchi (May 1989) PCR Applications, Issue 2 (Perkin Elmer-Cetus Users Bulletin). Cell samples for fetal testing can also be obtained from maternal peripheral blood using fluorescence-activated cell sorting, as described, e.g., by Iverson et al. (1981) Prenatal Diagnosis 9:31–48.

The method of the invention involves the specific amplification of target polynucleotides by PCR or ligation-based amplification to provide templates for the subsequent OLA. Ligation-based polynucleotide amplification, such as ligase chain reaction, is disclosed in the following references: Barany, PCR Methods and Applications 1: 5–16 (1991); Landegren et al, U.S. Pat. No. 4,988,617; Landegren et al, Science 241: 1077–1080 (1988); Backman et al, European patent publication 0439182A2; Yu and Wallace, Genomics 4: 560–569 (1989); and the like.

The PCR method for amplifying target polynucleotides in a sample is well known in the art and has been described by Saiki et al. (1986) Nature 324:163, as well as by Mullis in U.S. Pat. No. 4,683,195, Mullis et al. in U.S. Pat. No. 4,683,202, Gelfand et al. in U.S. Pat. No. 4,889,818, Innis et al. (eds.) PCR Protocols (Academic Press, N.Y. 1990), and Taylor (1991) Polymerase chain reaction: basic principles and automation, in PCR: A Practical Approach, McPherson et al. (eds.) IRL Press, Oxford.

Briefly, the PCR technique involves preparation of oligonucleotide primers which flank the target nucleotide sequence to be amplified, and are oriented such that their 3' ends face each other, each primer extending toward the other. The polynucleotide sample is extracted and denatured, preferably by heat, and hybridized with the primers which are present in molar excess. Polymerization is catalyzed in the presence of deoxyribonucleotide triphosphates (dNTPs) as noted above. This results in two "long products" which contain the respective primers at their 5' ends covalently linked to the newly synthesized complements of the original strands. The reaction mixture is then returned to polymerizing conditions, e.g., by lowering the temperature, inactivating a denaturing agent, or adding more polymerase, and a second cycle is initiated. The second cycle provides the two original strands, the two long products from the first cycle, two new long products replicated from the original strands, and two "short products" replicated from the long products. The short products have the sequence of the target sequence with a primer at each end. On each additional cycle, an additional two long products are produced, and a number of short products equal to the number of long and short products remaining at the end of the previous cycle. Thus, the number of short products containing the target sequence grow exponentially with each cycle. Preferably, PCR is carried out with a commercially available thermal cycler, e.g., Perkin Elmer model 9600 thermal cycler.

PCR amplification is carried out by contacting the sample with a composition containing first and second primers, sufficient quantities of the four deoxyribonucleotide triphosphates (dATP, dGTP, dCTP and dTTP) to effect the desired degree of sequence amplification, and a primer- and template dependent polynucleotide polymerizing agent, such as any enzyme capable of producing primer extension products, for example, *E. coli* DNA polymerase I, Klenow fragment of DNA polymerase I, T4 DNA polymerase, thermostable DNA polymerases isolated from *Thermus aquaticus* (Taq), which is available from a variety of sources (for example, Perkin Elmer), *Thermus thermophilus* (United States Biochemicals), *Bacillus stereothermophilus* (Bio-Rad), or *Thermococcus litoralis* ("Vent" polymerase, New England Biolabs), and the like.

An important feature of the invention is the selection of parameters in the amplification phase that results in well-resolved amplification products, e.g. as measured by well-resolved bands on an electrophoretic gel. The quality of the ligation products produced in the ligation phase are directly dependent on the quality of the amplification products. In this regard, an important parameter in PCR amplification is the annealing temperature employed. Preferably, the highest practical annealing is employed so that highly specific amplification is achieved and amplification of spurious targets is minimized.

After amplification, the temperature of the reaction mixture is lowered to implement OLA. The amount the temperature is lowered, of course, depends on the particular embodiment. Typically, the temperature is lowered from 20° C. to 50° C. to a second annealing temperature which facilitates specific annealing of the oligonucleotide probes to the target polynucleotide. That is, the second annealing temperature should be high enough to preclude the formation of duplexes having mismatches between oligonucleotide probes and the target polynucleotides. The OLA reaction for detecting mutations exploits the fact that the ends of two single strands of DNA must be exactly aligned for DNA ligase to join them. If the terminal nucleotides of either end are not properly base-paired to the complementary strand, then the ligase cannot join them. Thus, for a chosen target oligonucleotide sequence, first and second oligonucleotide probes are prepared in which the terminal nucleotides are respectively complementary to the normal sequence and the mutant sequence.

Whenever PCR amplification is employed, an important feature of the invention is providing oligonucleotide probes with 3' termini which are incapable of being extended by DNA polymerases. This is accomplished in a variety of conventional ways. For probes having a 3' terminus which will not be ligated, blocking is conveniently effected by attaching a blocking group, e.g. a fluorescent dye, 3' phosphate, 3' amino, or like group, or by providing a probe having dideoxynucleotide at the 3' terminus. For probes having a 3' hydroxyl that will be ligated, the probe to which it will be ligated can be provided in a concentration to effectively displace any polymerase in the reaction mixture, thereby precluding extension.

In a preferred embodiment, one of the first or second oligonucleotide probes bears a fluorescent label such as 5-carboxyfluorescein (5-FAM), 6-carboxyfluorescein (6-FAM), 2',7'-dimethoxy-4',5'-dichloro-6-carboxyfluorescein (JOE), N,N,N',N'-tetramethyl-6-carboxy rhodamine (TAMRA), 6-carboxy-X-rhodamine (ROX), 4,7,2',4',5',7'-hexachloro-6-carboxy-fluorescein (HEX-1), 4,7,2',4',5',7'-hexachloro-5-carboxy-fluorescein (HEX-2), 2',4',5',7'-tetrachloro-5-carboxyfluorescein (ZOE), 4,7,2',7'-tetrachloro-6-carboxy-fluorescein (TET-1), 1',2',7',8'-dibenzo-4,7-dichloro-5-carboxyfluorescein (NAN-2), and 1',2',7',8'-dibenzo-4,7-dichloro-6-carboxyfluorescein. In addition, ligation products may be detected by ELISA, sandwich-type nucleotide hybridization assays as described in U.S. Pat. No. 4,868,105 to Urdea, or other methods which will be readily apparent to those of skill in the art. The first and second oligonucleotide probes are constructed to hybridize to adjacent nucleic acid sequences in a target polynucleotide. Thus, the orientation of the first oligonucleotide probes relative to the second oligonucleotide probes may be 5' to 3', as depicted in FIG. 1, or 3' to 5'.

Preferably, oligonucleotide probes are fluorescently labeled by linking a fluorescent molecule to the non-ligating terminus of the probe. In order to facilitate detection in a multiplex assay, copies of different OLA reporter probes are labeled with different fluorescent labels. Guidance for selecting appropriate fluorescent labels can be found in Smith et al. (1987) Meth. Enzymol. 155:260–301, Karger et al. (1991) Nucl. Acids Res. 19:4955–4962, Haugland (1989) Handbook of Fluorescent Probes and Research Chemicals (Molecular Probes, Inc., Eugene, Oreg.). Preferred fluorescent labels include fluorescein and derivatives thereof, such as disclosed in U.S. Pat. No. 4,318,846 to Khanna et al. and Lee et al. (1989) Cytometry 10:151–164, and 6-FAM, JOE, TAMRA, ROX, HEX-1, HEX-2, ZOE, TET-1 or NAN-2, as described above, and the like. Most preferably, when a plurality of fluorescent dyes are employed, they are spectrally resolvable, as taught by Fung, supra. As used herein, "spectrally resolvable" fluorescent dyes are those with quantum yields, emission bandwidths, and emission maxima that permit electrophoretically separated polynucleotides labeled therewith to be readily detected despite substantial overlap of the concentration bands of the separated polynucleotides.

In a preferred embodiment, the first oligonucleotide probes are complementary to variant nucleotide sequences which are 5' to the sequence to which the second oligonucleotide probe is complementary. Ligation occurs, if at all, between the 3' terminus of the first oligonucleotide probe and the 5' terminus of the second oligonucleotide probe. Therefore, in this embodiment, first oligonucleotide probes bear mobility modifiers, or detectable labels, on their 5' terminus. The 5' mobility modifiers, e.g., non-complementary nucleotide or non-nucleotide extensions are not affected by the 5' to 3' exonuclease activity of Taq polymerase because conditions are such that the extensions are not annealed during amplification. Also, they are present in sufficiently low concentrations to prevent appreciable exonuclease activity should annealing occur. In this preferred embodiment, detection may be achieved by coupling a detectable label to the 3' terminus of the second oligonucleotide probe. This allows detection of the ligated product and also acts to block 3' extension by Taq polymerase. Extension from the 3' end of the first oligonucleotide probe may occur but it is not detected because it prevents ligation.

The reaction buffer used in the method of the invention must support the requirements of both the amplification scheme employed and OLA. Taq DNA ligase requires NAD+ as a cofactor, the divalent cation Mg2+ for activity, and its activity is stimulated by low concentrations of the monovalent cation K+ but not Na+ (Takahashi et al. (1984) J. Biol. Chem. 259:10041–10047). Optimal assay conditions for OLA reactions require 5 to 10 mM magnesium ions in the presence of 10 to 50 units of thermostable ligase. Thus, a reaction buffer which will find utility with the claimed coupled amplificationligation method is made up of, inter alia, 1 to 200 mM, preferably 25 to 50 mM, K+, 0.5 to 20 mM, preferably 1 to 5 mM Mg2+, and 0.5 to 20 mM, preferably 1 to 5 mM, NAD+.

Preferably, the method of the invention is carried out as an automated process which utilizes a thermostable enzyme. In this process the reaction mixture is cycled through PCR cycles, e.g., a denaturing region, a primer annealing region and a reaction region, and then through one or more OLA cycles. A machine may be employed which is specifically adapted for use with a thermostable enzyme, which utilizes temperature cycling without a liquid handling system, since the enzyme need not be added at every cycle.

As mentioned above, the invention includes kits for carrying out the method. Such kits include (a) a plurality of amplification primers, each amplification primer of the plurality being capable of annealing to one or more target polynucleotides at a first annealing temperature; (b) a plurality of oligonucleotide probes, each oligonucleotide probe being capable of annealing to the target polynucleotides at a second annealing temperature, such that substantially none of the oligonucleotide probes anneal to the target polynucleotide at the first annealing temperature; (c) means for amplifying the target polynucleotides using the plurality of amplification primers at a temperature greater than or equal to the first annealing temperature; and (d) means for ligating oligonucleotide probes at a temperature equal to or less than the second annealing temperature to form one or more ligation products. Preferably, kits of the invention further include instructions pertinent for the particular embodiment of the kit, such instructions describing the oligonucleotide probes and amplification primers included and the appropriate first and second annealing temperatures for operation of the method. In the case of PCR amplification, kits further include a DNA polymerase, nucleoside triphosphates, a DNA ligase, and reaction buffer for the coupled ligation and amplification. Most preferably, oligonucleotide probes and amplification primer of the kit are selected from the sequences of Tables 1 and 2 for analyzing the CFTR locus.

EXPERIMENTAL

The following examples are put forth so as to provide those of ordinary skill in the art with a complete disclosure and description of how to carry out the method of the invention, and are not intended to limit the scope of that which the inventors regard as their invention. Unless indicated otherwise, parts are parts by weight, temperature is in °C. and pressure is at or near atmospheric.

The detection and distinction of allelic variants of the cystic fibrosis transmembrane conductance regulator (CFTR) gene by method of the invention is exemplified. This method can detect all types of single base substitution mutations in addition to small deletions and insertions. The technique involves an initial PCR amplification of small segments (individual exons or intronic fragments) of the CFTR gene, followed by an oligonucleotide ligation reaction which thereby allows the simultaneous screening for a number of mutations within each amplified region. In the OLA procedure two juxtaposed synthetic oligonucleotide probes hybridizing to a target DNA strand are enzymatically joined by thermostable DNA ligase only if there is correct base pairing at the junction region of the two hybridizing probes. To distinguish between two alternative DNA sequences, three oligonucleotide probes were used as shown in FIG. 1. Normal and mutant diagnostic OLA probes were designed such that their 3' terminal base was homologous to either the normal or the altered base of a particular mutation under study. The allele-specific oligonucleotides were modified at their 5' termini by addition of different sized non-complementary tails to enable identification of different allelic products by size in polyacrylamide gels. The reporter oligonucleotide probe, designed to hybridize immediately downstream of the two allelic or discriminating probes, was 5'-phosphorylated and modified by the addition of the fluorescent dye 5-FAM to its 3' end. Repeated thermocycling between the annealing temperature of the oligonucleotide probes, i.e., the second annealing temperature in this embodiment, and a denaturation temperature for the probes resulted in linear amplification of ligation products. The ligation products were then analyzed by electrophoresis on 8% denaturing polyacrylamide gels on the Applied Biosystems Model 373A DNA sequencer.

Human genomic DNA was prepared from peripheral blood nucleated cells and buccal cells. DNA was isolated from whole blood using the guanidinium method for extracting DNA (Chirgwin et al. (1979) Biochemistry 18:5294–5296; Chehab et al. (1992), supra). Briefly, 3 to 5 ml of stabilized whole blood (ethylene diamine tetraacetate (EDTA) or citrate) was mixed with 45 ml of lysis solution (0.32 M sucrose, 10 mM Tris HCl, pH 8.0, 5 mM MgCl2, 1% TRITON (polyethylene glycol tert-octylphenyl ether X-100) and nuclei were pelleted by centrifugation at 1500 rpm for 20 min. Nuclei were resuspended in 2 ml of guanidinium thiocyanate (5 M guanidine thiocyanate, 50 mM Tris HCl, pH 8.0, 10 mM EDTA), extracted by rotation for 15 min, and DNA was precipitated by addition of an equal volume of isopropyl alcohol. Purified DNA was dissolved in a small volume of TE buffer (10 mM Tris HCl, pH 8.0, 1 mM EDTA) or sterile water.

Cells from the mucosal surface of the buccal cavity were obtained by gently scraping with a brush or toothpick. After collection entrapped buccal cells were dislodged by gentle agitation into 500 µl of PBS in a microcentrifuge tube and pelleted by centrifugation at 1200 g for 5 min. DNA was either extracted from buccal cells as described above or by resuspending the cells in a 50 to 200 µl volume of sterile water and boiling for 20 min. Cell debris was removed by brief centrifugation, and 5 µl of the supernatant DNA solution was used in DNA amplification reactions. In some cases, samples were digested with proteinase K (100 µg/ml) for several hr at 50° C. before boiling.

All oligonucleotides used were synthesized by an Applied Biosystems Model 394 DNA synthesizer (Foster City, Calif.) using standard cyanoethyl phosphoramidite chemistry (Giusti et al. (1993) PCR Methods Applic. 2:223–227).

Reporter oligonucleotide probes were synthesized with 3' Amine-ON CPG columns (5220-1, Clontech Laboratories, Inc., Palo Alto, Calif.) to derivatize the 3' end for subsequent labeling with the fluorescent dye, such as 5-carboxy-fluorescein (FAM), 2',7'dimethoxy-4',5'-dichloro-6-carboxy-fluorescein, N,N,N',N'-tetramethyl-6-carboxy rhodamine, 6-carboxyrhodamine X, or the like. The 5' end of each reporter oligonucleotide probe was phosphorylated using 5' Phosphate-ON (5210-1, Clontech Laboratories, Inc., Palo Alto, Calif.) to chemically phosphorylate the 5' terminus. Dye-labeled, phosphorylated oligonucleotides were purified from nonconjugated oligonucleotides by reverse-phase HPLC (Giusti et al., supra). Normal and mutant allelic oligonucleotide probes were purified using oligonucleotide purification cartridges (Applied Biosystems). Purified oligonucleotide probes were lyophilized, resuspended in sterile distilled water, and quantified spectrophotometrically. Sequences of primers and probes used in the Example provided below are depicted in Tables 1 and 2. Some primer and probe sequences are taken from Zielenski et al, Genomics, 10: 214–228 (1991).

TABLE 1

PCR PRIMERS

| | Primer Sequence (5'–3')[a] | $T_m$ (° C.)[b] | Region Amplified[c] | Size (bp)[d] |
|---|---|---|---|---|
| SEQ. ID NO.: 59 | GAATGGGATA GAGAGCTGGC TTCAAAGAAA AATCCT | 81.5 | Exon 3 | 213 |
| SEQ. ID NO.: 60 | CCTTTATATT TTTACACCTA TTCACCAGAT TTCGTAGTC | 76.3 | | |
| SEQ. ID NO.: 1 | AGAGTTTCAA CATATGGTAT GACCCTC | 66.6 | Exon 4 | 451 |
| SEQ. ID NO.: 2 | CCCTTACTTG TACCAGCTCA CTACCTA | 68.6 | | |
| SEQ. ID NO.: 49 | ATTTCTGCCT AGATGCTGGG AAATAAAAC | 70.6 | Exon 5 | 402 |
| SEQ. ID NO.: 50 | CCAGGAAAAC TCCGCCTTTC CAGTTG | 78.3 | | |
| SEQ. ID NO.: 51 | CTCTAGAGAC CATGCTCAGA TCTTCCAT | 68.7 | Exon 7 | 416 |
| SEQ. ID NO.: 52 | GCAAAGTTCA TTAGAACTGA TCTATTGACT | 68.5 | | |
| SEQ. ID NO.: 53 | TATACAGTGT AATGGATCAT GGGCCATGT | 82.0 | Exon 9 | 578 |
| SEQ. ID NO.: 54 | GTGCAAGATA CAGTGTTGAA TGTGGTGCA | 76.6 | | |
| SEQ. ID NO.: 3 | GTGCATAGCA GAGTACCTGA AACAGGAAGT A | 71.8 | Exon 10 | 503 |
| SEQ. ID NO.: 4 | TGATCCATTC ACAGTAGCTT ACCCATAGAG G | 67.7 | | |
| SEQ. ID NO.: 5 | CAACTGTGGT TAAAGCAATA GTGTGATTAT ATGATTA | 67.9 | Exon 11 | 425 |
| SEQ. ID NO.: 6 | GCACAGATTC TGAGTAACCA TAATCTCTAC CAAATC | 67.7 | | |
| SEQ. ID NO.: 55 | GTGAATCGAT GTGGTGACCA TATTGTAATG CATGTA | 67.7 | Exon 12 | 339 |
| SEQ. ID NO.: 56 | ACCATGCTAC ATTCTGCCAT ACCAACAATG GTGAAC | 83.6 | | |
| SEQ. ID NO.: 57 | CTCATGGGAT GTGATTCTTT CGACCAATTT AGTG | 75.9 | Exon 13 | 297 |
| SEQ. ID NO.: 58 | AGAATCTGGT ACTAAGGACA GCCTTCTCTC TAA | 74.0 | | |
| SEQ. ID NO.: 7 | CATCACAAAT AATAGTACTT AGAACACCTA GTACAGCTGC T | 76.4 | Exon 14b | 476 |
| SEQ. ID NO.: 8 | GCCCTGAACT CCTGGGCTCA AGTGATCCTC CTGC | 78.1 | | |
| SEQ. ID NO.: 9 | AATTATAATC ACCTTGTGGA TCTAAATTTC AGTTGACTTG TC | 79.1 | Intron 19 | 300 |
| SEQ. ID NO.: 10 | TTTAAGACAT ACCCTAAATC TAAGTCAGTG TTTTCTAATA AC | 76.4 | | |
| SEQ. ID NO.: 11 | GCCCGACAAA TAACCAAGTG ACAAATAG | 73.9 | Exon 19 | 454 |
| SEQ. ID NO.: 12 | GCTAACACAT TGCTTCAGGC TACTGGG | 75.0 | | |
| SEQ. ID NO.: 13 | GGTCAGGATT GAAAGTGTGC AACAAGGTTT GAATGAATAA G | 84.7 | Exon 20 | 473 |
| SEQ. ID NO.: 14 | CTATGAGAAA ACTGCACTGG AGAAAAAAAA GACAGCAATG | 82.7 | | |
| SEQ. ID NO.: 15 | AATGTTCACA AGGGACTCCA AATATTGCTG TAGTATTTG | 80.2 | Exon 21 | 483 |
| SEQ. ID NO.: 16 | TCCAGTCAAA AGTACCTGTT GCTCCAGGTA TGTTAGGGTA | 83.7 | | |

[a]Primer sequences indicated in bold text are from Zielenski, et al.
[b]$T_m$ values were calculated by nearest neighbor analysis.
[c]Region of the CFTR gene amplified.
[d]PCR product size in base pairs.

TABLE 2

Oligonucleotide Probes for Detection of CF Mutations

| Mutation | Wild-Type Probe (5′–3′)[a] | Mutant Probe (5′–3′)[a] | Common Probe (5′–3′)[a] | Ligation Probe Size (bases) Wild-Type | Ligation Probe Size (bases) Mutant |
|---|---|---|---|---|---|
| ΔF508 | $(a_{21})$-CACCATTAAAGAAAATATCATCTT Seq. ID No. 33 | $(a_{20})$-GGCACCATTAAAGAAAATATCAT Seq. ID No. 17 | TGGTGTTTCCTATGATGAATAT Seq. ID No. 61 | 67 | 65 |
| | $(a_3)$-CACCATTAAAGAAAATATCATCTT Seq. ID No. 34 | $(a_2)$-GGCACCATTAAAGAAAATATCAT Seq. ID No. 18 | | 49 | 47 |
| G542X | GTGATTCCACCTTCTCC Seq. ID No. 35 | GTGTGATTCCACCTTCTCA Seq. ID No. 19 | AAGAACTATATTGTCTTTCTCT Seq. ID No. 62 | 39 | 41 |
| G551D | $(a_2)$-TAAAGAAATTCTTGCTCGTTGAC Seq. ID No. 36 | TAAAGAAATTCTTGCTCGTTGAT Seq. ID No. 20 | CTCCACTCAGTGTGATTCCA Seq. ID No. 63 | 45 | 43 |
| W1282X | $(a_5)$-TATCACTCCAAAGGCTTTCCTC Seq. ID No. 37 | $(a_7)$-TATCACTCCAAAGGCTTTCCTT Seq. ID No. 21 | CACTGTTGCAAAGTTATTGAATCC Seq. ID No. 64 | 51 | 53 |
| N1303K | $(c_7)$-TATTTTTCTGGAACATTTAGAAAAAAAC Seq. ID No. 38 | $(c_6)$-TATTTTTCTGGAACATTTAGAAAAAAG Seq. ID No. 22 | TTGGATCCCTATGAACACTGAAG Seq. ID No. 85 | 55 | 57 |
| 3905InsT | $(a_{10})$-AAGAGTACTTTGTTTATCAGCTTTTTT Seq. ID No. 39 | $(a_{12})$-AAGAGTACTTTGTTTATCAGCTTTTTTT Seq. ID No. 23 | GAGACTACTGAACACTGAAGGAG Seq. ID No. 66 | 59 | 62 |
| 3849 + 10kbC->T | $(a_{25})$-ATCTGTTGCAGTAATAAAATGGC Seq. ID No. 40 | $(a_{26})$-CATCTGTTGCAGTAATAAAATGGT Seq. ID No. 24 | GAGTAAGACACCCTGAAAGGAA Seq. ID No. 67 | 70 | 72 |
| 3849 + 4A->G | $(a)$-CCTGGCCAGAGGGTGA Seq. ID No. 41 | CTGGCCAGAGGGTGG Seq. ID No. 25 | GATTTGAACACTGCTTGCT Seq. ID No. 68 | 36 | 34 |
| 3659delC | $(a_2)$-CAACAGAAGGTAAACCTAC Seq. ID No. 42 | CCAACAGAAGGTAAACCTA Seq. ID No. 26 | CAAGTCAACCAAACCATACA Seq. ID No. 69 | 41 | 39 |
| R1171 | ACTAGATAAATCGCGATAGAGC Seq. ID No. 43 | $(a_2)$-ACTAGATAAATCGCGATAGAGT Seq. ID No. 27 | GTTCCTCCTTGTTATCCGGGT Seq. ID No. 70 | 43 | 45 |
| R1162X | $(a)$-TTTCAGATGCGATCTGTGAGCC Seq. ID No. 44 | $(a_3)$-TTTCAGATGCGATCTGTGAGCT Seq. ID No. 28 | GAGTCTTTAAGTTCATTGACATGC Seq. ID No. 71 | 47 | 49 |
| 1717-1G->A | $(a_4)$4CTGCAAACTTGGAGATGTCT Seq. ID No. 45 | $(a_6)$TCTGCAAACTTGGAGATGTCT Seq. ID No. 29 | TATTACCAAAAATAGAAAATTAGAGA Seq. ID No. 12 | 51 | 53 |
| 621 + 1G->T | $(a_7)$TATGTTTAGTTTGATTTATAAGAAGG Seq. ID No. 46 | $(a_8)$-TATGTTTAGTTTGATTTATAAGAAGT Seq. ID No. 30 | TAATACTTCCTTGCACAGGCCC Seq. ID No. 73 | 55 | 57 |
| R553X | $(a_{18})$-TGCTAAAGAAATTCTTGCTCG Seq. ID No. 47 | $(a_{20})$-TTGCTAAAGAAATTCTTGCTCA Seq. ID No. 31 | TTGACCTCCACTCAGTGTGA Seq. ID No. 74 | 59 | 6 |
| 2789 + 5G->A | $(c_{27})$-CACAATAGGACATGGAATAC Seq. ID No. 48 | $(c_{25})$-CACAATAGGACATGGAATAT Seq. ID No. 32 | TCACTTTCCAAGGAGCCAC Seq. ID No. 75 | 60 | 64 |

[a]5′-Poly(a) or poly(c) extensions were added to wild-type and mutant probes for multiplex detection of alleles by gel electrophoresis.
[b]Probes were 5′-phosphorylated and fluorescently labeled at their 3′-ends with the fluoroscein dye FAM.

EXAMPLE 1

Analysis of the Fifteen Most Common Cystic Fibrosis Mutations with Coupled Amplification and Ligation The method of performing a multiplex polymerase chain reaction (PCR) and ligase amplification reaction (OLA) uses PCR primers with high Tm's (76° C. to 116° C.), OLA oligonucleotides with Tm's between 52° C. to 68° C., a two-step PCR cycle that employs a denaturation step done at 94° C. and an annealing elongation step done at 72° C., and one to three two-step OLA cycles that have a denaturation step done at 94° C. and a hybridization step done at between about 52° C. to 56° C. Coupled amplification-ligation reactions were performed in a total volume of 50 µl in 0.2 ml thin-wall tubes in a Perkin-Elmer 9600 DNA thermocycler. Each reaction contained 2 µl of DNA (100–200 ng) extracted from peripheral blood or 2 µl of DNA from boiled mucosal cell lysates, primers for multiplex PCR (200–800 nM) of CFTR exons 10, 11, 20, 21 and intron 19, or CFTR exons 4, 11, 14b and 19, and oligonucleotide probes (2.5–12.5 nM) for CFTR mutations G542X, G551D, ΔF508, W1282X, N1303, 3905insT and 3849+10kbCT, or 3849+4AG, 3659delC, R117H, R1162X, 117–1GT, 621+1GT R553X and 2789+5GA, respectively, in buffer containing 10 mM Tris HCl, pH 8.3, 50 mM KCl, 4.5 mM MgCl2, 1 mM NAD+, 200–600 µM each dATP, dCTP, dGTP and dTTP, 5 units cloned Taq DNA polymerase and 20 units of Thermus aquaticus DNA ligase (Barany et al. (1991), supra).

Following a 5 min denaturation at 94° C., samples were subjected to 25 PCR amplification cycles each consisting of 94° C. for 30 sec and 72° C. for 1.5 min. This was followed by a second denaturation at 98° C. for 3 min and then 1–10 oligonucleotide ligation cycles of 94° C. for 30 sec and 55° C. for 3 min. Samples were stored, if at all, at -20° C. following the method and prior to analysis.

Amplification-ligation products were analyzed by taking a 0.5–2.0 µl aliquot of each reaction mixture, 10 fmol of internal lane standard consisting of oligomers of 30 to 70 bases in size labeled with the dye ROX (6-carboxyrhodamine X) (Applied Biosystems) and 4 µl formamide loading buffer (deionized formamide:50 mM EDTA, 5:1 (v/v)). Samples were heat denatured at 100° C. for 5 min, rapidly cooled on ice and loaded onto an 8% polyacrylamide denaturing sequencing gel. Gels were electrophoresed for 3 hr at 1500 V in an Applied Biosystem Model 373A fluorescent DNA sequencer. The location and relative quantity of ligation products were automatically recorded with Genescan 672 software (Applied Biosystem). PCR products were analyzed by electrophoresis in 3% MetaPhor agarose (FMC BioProducts, Rockland, Me.) gels in 1× Tris-borate EDTA (TBE) buffer (0.09 M Tris-borate, 0.002 M EDTA, pH 8.0) at 100 V for 5–6 hours and visualized by staining with 0.5 µg/ml ethidium bromide.

Figure 2A:
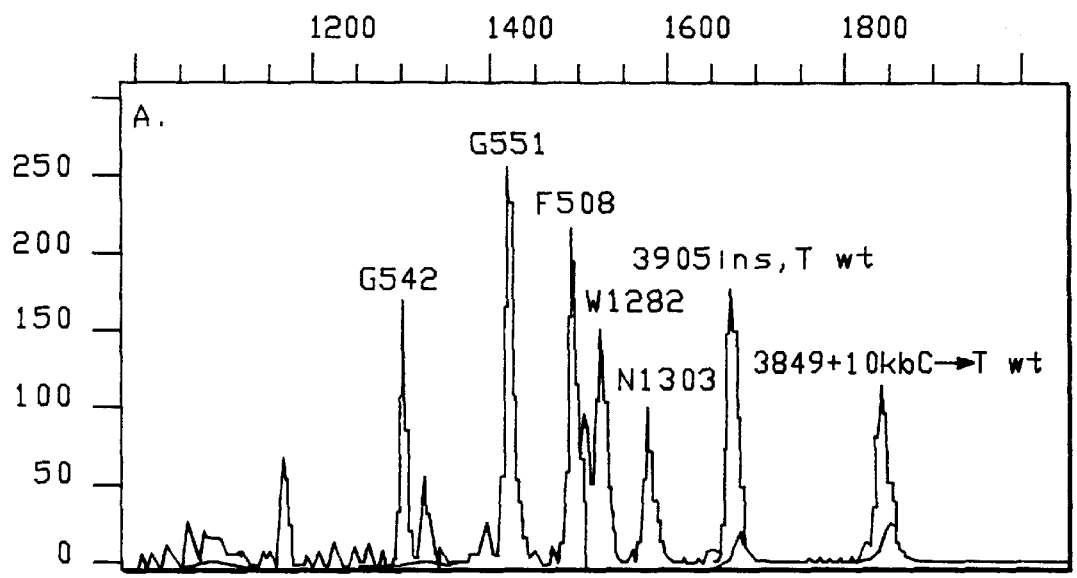
FIGS. 2A and 2B are electropherograms of fluorescently labeled ligation products.
Figure 2B:
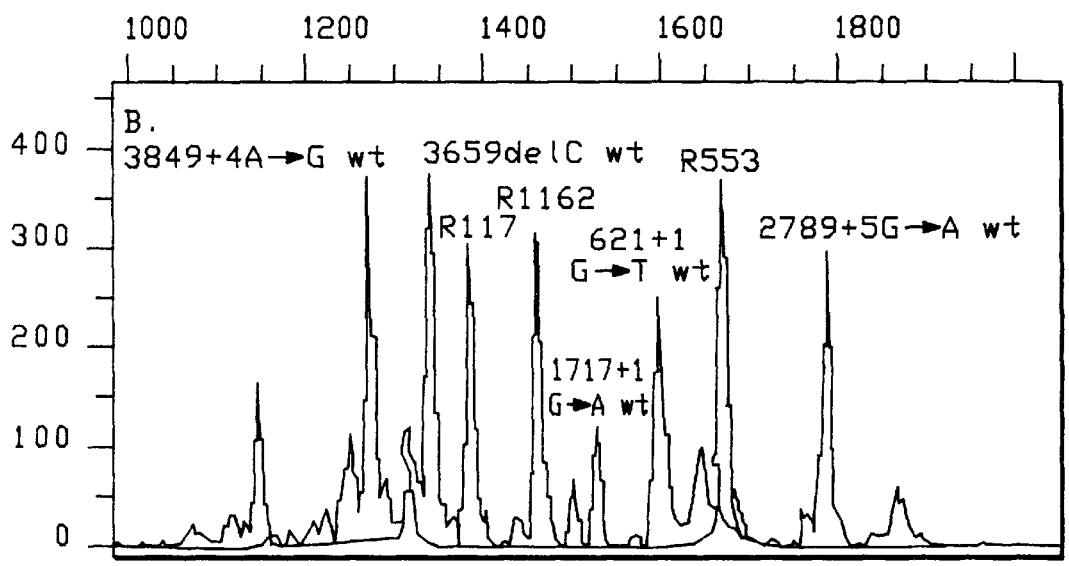

FIG. 2 depicts the results of these assays. FIGS. 2A and 2B show the ability of the assay to accurately discriminate 7 and 8, respectively, of the 15 most common cystic fibrosis mutations.

I claim:

1. A method for detecting a target polynucleotide in a sample comprising:

amplifying the target polynucleotide by primer extension to form an amplification product that is complementary to the target polynucleotide, the amplification being performed (a) in the presence of at least one pair of oligonucleotide probes capable of hybridizing to contiguous sequences of the amplification product; and (b) at a higher temperature than a melting point temperature of the oligonucleotide probes;

ligating those oligonucleotide probes which hybridize to contiguous sequences of the amplification product to form a ligation product; and detecting the ligation product.

2. The method according to claim 1 wherein the at least one pair of oligonucleotide probes include a first oligonucleotide probe and a second oligonucleotide probe which hybridizes to the target polynucleotide 3' relative to the first oligonucleotide probe, the second oligonucleotide probe including a moiety at a 3' end which prevents extension of the second oligonucleotide probe by a polymerase.

3. The method according to claim 2 wherein the moiety which prevents extension of the second oligonucleotide probe is a detectable marker.

4. The method according to claim 1 wherein the at least one pair of oligonucleotide probes include a first oligonucleotide probe and a second oligonucleotide probe which hybridizes to the target polynucleotide 3' relative to the first oligonucleotide probe, the first oligonucleotide probe including a moiety attached to a 5' end which does not hybridize to the amplification product and modifies the mobility of the ligation product in a size dependent separation process, the method further including the step of isolating the ligation product by a size dependent separation process.

5. The method according to claim 4 wherein the mobility modifier is a polymer chain.

6. The method of claim 1 wherein the step of amplifying is performed at a temperature between about 72° C. and about 84° C. and the step of ligating is performed at a temperature between about 30° C. and about 55° C.

7. The method of claim 1 wherein the step of amplifying is performed at a temperature between about 72° C. and about 75° C. and the step of ligating is performed at a temperature between about 40° C. and about 55° C.

8. A method for detecting a plurality of target polynucleotides in a sample comprising:
    amplifying the plurality of target polynucleotides by primer extension to form a plurality of amplification products that are complementary to the plurality of target polynucleotides, the amplification being performed (a) in the presence of a plurality of pairs of oligonucleotide probes capable of hybridizing to contiguous sequences of the amplification products, and (b) at a higher temperature than a melting point temperature of the oligonucleotide probes;
    ligating those oligonucleotide probes which hybridize to contiguous sequences of the plurality of amplification products to form a plurality of ligation products; and
    detecting the plurality of ligation products.

9. The method of claim 8 wherein the plurality of ligation products each have a different fluorescent label, and the step of detecting includes detecting a fluorescent signal generated by the different fluorescent labels.

10. The method of claim 9 wherein the fluorescent labels are selected from the group consisting of 5-carboxyfluorescein, 6-carboxyfluorescein, 2',7'-dimethoxy-4',5'-dichloro-6-carboxyfluorescein, N,N,N',N'-tetramethyl-6-carboxy rhodamine, 6-carboxyrhodamine X, 4,7,2',4',5',7'-hexachloro-6-carboxyfluorescein, 4,7,2',4',5',7'-hexachloro-5-carboxyfluorescein, 2',4',5',7'-tetrachloro-5-carboxyfluorescein, 4,7,2',7'-tetrachloro-6-carboxyfluorescein, 1',2',7',8'-dibenzo-4,7-dichloro-5-carboxyfluorescein, and 1',2',7',8'-dibenzo-4,7-dichloro-6-carboxyfluorescein.

11. The method of claim 8 wherein the plurality of ligation products each have a distinct electrophoretic mobility and the stop of detecting includes separating the plurality of ligation products by a size dependent separation process.

12. The method according to claim 11 wherein the plurality of pairs of oligonucleotide probes each include a first oligonucleotide probe and a second oligonucleotide probe which hybridizes to the target polynucleotide 3' relative to the first oligonucleotide probe, the first oligonucleotide probe including a moiety attached to a 5' end which does not hybridize to the amplification product and modifies the mobility of the ligation product in a size dependent separation process.

13. The method according to claim 12 wherein the mobility modifier is a polymer chain.

14. The method according to claim 13 wherein the polymer chain includes polyethylene oxide or polypropylene subunits.

15. The method of claim 12 wherein the plurality of ligation products each have a different fluorescent label, and the step of detecting includes detecting a fluorescent signal generated by the different fluorescent labels.

16. The method of claim 8 wherein the plurality of target polynucleotides are alleles or mutations of the gene encoding cystic fibrosis transmembrane conductance regulator (CFTR).

17. The method of claim 16 wherein the plurality of target polynucleotides are alleles or mutations of the gene encoding cystic fibrosis transmembrane conductance regulator (CFTR) selected from the group consisting of ΔF518, G542X, G551D, W1282X, N1303K 3905insT, 3849+10kbCT, 3849+4AG, 3659delC, R117H, R1162X, 1717–1GA, 621+1GT, R553X, 2789+5GA, R347P, 2184delA, 1078delT, R334W, 711+1GT, G85E, 1898+1GA, A455E, S549R, S549N, R560T, Δl517, Q493X, V520F and Y122X.

18. The method of claim 8 wherein the step of amplifying is performed at a temperature between about 72° C. and about 84° C. and the step of ligating is performed at a temperature between about 30° C. and about 55° C.

19. The method of claim 8 wherein the step of amplifying is performed at a temperature between about 72° C. and about 75° C. and the step of ligating is performed at a temperature between about 40° C. and about 55° C.

20. A kit for detecting a target polynucleotide of known sequence in a sample comprising:
    a sufficient quantity of amplification primers to perform an amplification reaction on the target polynucleotide to form an amplification product; and
    a sufficient quantity of two isolated oligonucleotide probes capable of hybridizing to contiguous sequences of the amplification product to perform a ligation reaction on the oligonucleotide probes, the amplification primers having a melting point temperature sufficiently high to enable performance of the amplification reaction at a temperature above the melting point temperature of the oligonucleotide probes.

21. The kit according to claim 20 wherein the isolated amplification primers have a sequence of about 30–50 nucleotides and melting point temperature of at least 80° C. and the isolated oligonucleotide probes have a sequence of about 8–30 nucleotides and a melting point temperature less than 70° C.

22. The kit according to claim 20 wherein one of the oligonucleotide probes includes a fluorescent label.

23. The kit according to claim 20 where the two oligonucleotide probes include a first oligonucleotide probe and a second oligonucleotide probe which hybridizes to the target polynucleotide 3' relative to the first oligonucleotide probe, the second oligonucleotide probe including a moiety at a 3' end which prevents extension of the second oligonucleotide probe by the polymerase.

24. The kit according to claim 20 where the two oligonucleotide probes include a first oligonucleotide probe and a second oligonucleotide probe which hybridizes to the target polynucleotide 3' relative to the first oligonucleotide probe, the first oligonucleotide probe including a moiety attached to a 5' end which does not hybridize to the amplification product and modifies the mobility of the ligation product in a size dependent separation process.

25. The kit according to claim 24 wherein the mobility modifier is a polymer chain.

26. The kit according to claim 25 wherein the polymer chain includes polyethylene oxide or polypropylene subunits.

27. A kit for detecting a plurality of target polynucleotides of known sequence in a sample comprising:
    sufficient quantities of amplification primers to perform amplification reactions on the plurality of target polynucleotides to form a plurality of amplification products; and sufficient quantities of a plurality of pairs of isolated oligonucleotide probes capable of hybridizing to contiguous sequences of the plurality of amplification products to perform ligation reactions on the pairs of oligonucleotide probes, each amplification primer having a melting point temperature sufficiently high to enable performance of the amplification reactions at a temperature above a melting point temperature of the oligonucleotide probes.

28. The kit according to claim 27 wherein the isolated amplification primers have a sequence of about 30–50 nucleotides and a melting point temperature of at least 80° C. and the isolated oligonucleotide probes have a sequence of about 8–30 nucleotides and a melting point temperature less than 70° C.

29. The kit according to claim 27 where the pairs of oligonucleotide probes include a first oligonucleotide probe and a second oligonucleotide probe which hybridizes to the target polynucleotide 3' relative to the first oligonucleotide probe, the second oligonucleotide probe including a moiety at a 3' end which prevents extension of the second oligonucleotide probe by a polymerase.

30. The kit according to claim 27 where the pairs of oligonucleotide probes include a first oligonucleotide probe and second oligonucleotide probe which hybridizes to the target polynucleotide 3' relative to the first oligonucleotide probe, the first oligonucleotide probe including a moiety attached to a 5' end which does not hybridize to the amplification product and modifies the mobility of the ligation product in a size dependent separation process.

31. The kit according to claim 30 wherein the mobility modifier is a polymer chain.

32. The kit according to claim 30 wherein the polymer chain includes polyethylene oxide or polypropylene subunits.

33. The kit according to claim 27 wherein the plurality of target polynucleotides are alleles or mutations of a gene encoding cystic fibrosis transmembrane conductance regulator (CFTR), the isolated amplification primers being capable of hybridizing to contiguous sequences of the CFTR allele or mutation, the isolated oligonucleotide probes being capable of hybridizing to contiguous sequences of the plurality of amplification products.

34. The kit according to claim 33 wherein the allele or mutation of a gene encoding cystic fibrosis transmembrane conductance regulator (CFTR) is selected from the group consisting of ΔF508, G542X, G551D, W1282X, N1303K 3905insT, 3849+10kbCT, 3849+4AG, 3659delC, R117H, R1162X, 1717-1 GA, 621+1GT, R553X, 2789+5GA, R347P, 2184delA, 1078delT, R334W, 711+1GT, G85E, 1898+1GA, A455E, S549R, S549N, R560T, Δl507, Q493X, V520F and Y122X.

* * * * *